(12) United States Patent
Chaleff

(10) Patent No.: US 11,883,124 B2
(45) Date of Patent: Jan. 30, 2024

(54) DISPOSABLE MEDICAL DEVICE COVERS

(71) Applicant: Vicky Chaleff, St Petersburg, FL (US)

(72) Inventor: Vicky Chaleff, St Petersburg, FL (US)

( * ) Notice: Subject to any disclaimer, the term of this patent is extended or adjusted under 35 U.S.C. 154(b) by 158 days.

(21) Appl. No.: 17/444,128

(22) Filed: Jul. 30, 2021

(65) Prior Publication Data
US 2022/0031416 A1 Feb. 3, 2022

Related U.S. Application Data

(60) Provisional application No. 62/706,097, filed on Jul. 31, 2020.

(51) Int. Cl.
*A61B 46/10* (2016.01)
*A61B 46/00* (2016.01)

(52) U.S. Cl.
CPC .............. *A61B 46/10* (2016.02); *A61B 46/40* (2016.02)

(58) Field of Classification Search
CPC .......... A61B 46/10; A61B 46/20; A61N 2/00; A61N 2/02; A61N 2/06; A61N 2/12
See application file for complete search history.

(56) References Cited

U.S. PATENT DOCUMENTS

| | | | |
|---|---|---|---|
| 4,241,828 A | 12/1980 | Bourdelle et al. | |
| 4,723,912 A | 2/1988 | Nieusma | |
| 5,361,781 A * | 11/1994 | Antonini | A61M 25/02 128/853 |
| 5,907,877 A | 6/1999 | Allgood | |
| 6,497,233 B1 * | 12/2002 | DeAngelis | A61B 46/10 128/849 |
| 6,537,207 B1 | 3/2003 | Rice et al. | |
| 8,661,573 B2 | 3/2014 | Shafer et al. | |
| 9,199,063 B2 | 12/2015 | Baid | |
| 9,265,426 B2 | 2/2016 | Zuluage | |
| 9,561,079 B2 | 2/2017 | Perlman | |
| 9,839,488 B2 | 12/2017 | Ma | |
| 2005/0257996 A1 | 11/2005 | Brown et al. | |
| 2007/0267026 A1 | 11/2007 | Grant-Jennings | |
| 2009/0294313 A1 | 12/2009 | Pacey et al. | |
| 2012/0097176 A1 * | 4/2012 | Pitaoulis | A61B 46/27 128/856 |
| 2013/0263868 A1 | 10/2013 | Grenier | |
| 2014/0319000 A1 | 10/2014 | Fishberger et al. | |
| 2016/0022363 A1 | 1/2016 | Harttig et al. | |
| 2019/0099232 A1 * | 4/2019 | Soto | A61B 90/39 |
| 2020/0218307 A1 | 7/2020 | Pruter | |

* cited by examiner

*Primary Examiner* — Camtu T Nguyen
(74) *Attorney, Agent, or Firm* — Dunlap Bennett & Ludwig, PLLC

(57) ABSTRACT

A disposable cover for PEMFT medical devices and a method of making and using the same. The disposable cover is made from a fluidproof material that protects the user and the medical device by being a barrier therebetween. The disposable cover can be adapted for strap-based medical devices and disc-based medical devices, as well as other devices.

5 Claims, 5 Drawing Sheets

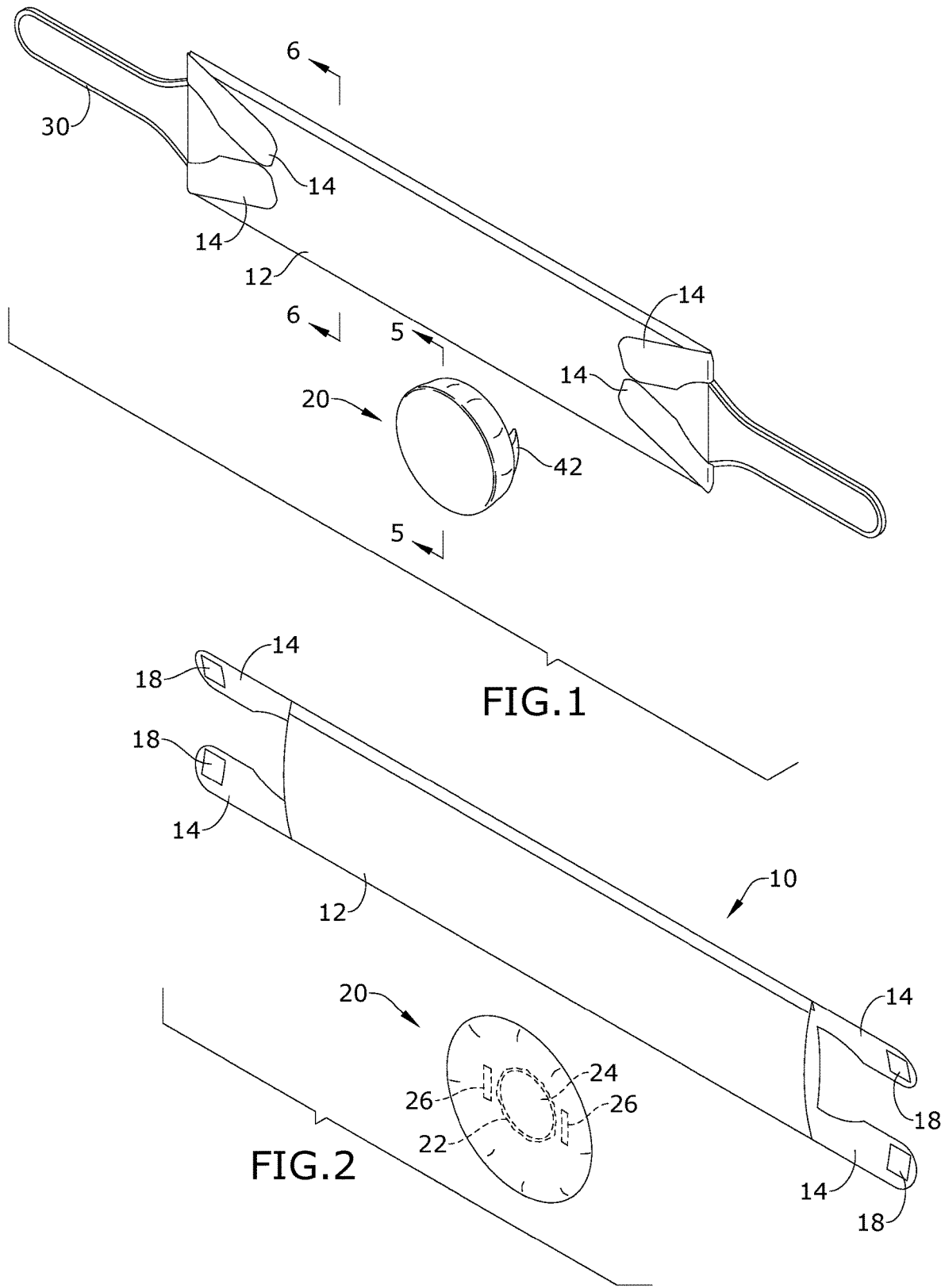

DISPOSABLE MEDICAL DEVICE COVERS

CROSS-REFERENCE TO RELATED APPLICATION

This application claims the benefit of priority of U.S. provisional application No. 62/706,097, filed 31 Jul. 2020, the contents of which are herein incorporated by reference.

BACKGROUND OF THE INVENTION

The present invention relates to medical devices, and more particularly to disposable medical device covers.

Pulsed electromagnetic field therapy (PEMFT, or PEMF therapy) uses electromagnetic fields aimed at healing certain ailments, including but not limited to non-union fractures and depression. These PEMFT applicators/medical devices offer non-invasive, painless treatment through one or more flat spiral coils energized by an operatively associated frequency generator so that the coils emit a pulsating, varying intensity and frequency electromagnetic field. Frequently, these medical devices include the PEMF coil(s) at least partially embedded in a material suitable to be placed on the skin of a patient; and the medical device is sometimes made wearable by way of being embodied in a strap or the like. Accordingly, the exterior of the medical device that interfaces with the patient is sheath in a material that is accordingly "skin-safe".

The frequent public use from medical and non-medical practices, at home use, and normal handling can spread infection, disease, bodily fluids and organisms from one to another if the medical device strap and disc applicators are not covered and so can cause the current skin-safe material to become soiled with sweat, bodily fluid particulates, and the like. As a result, normal handling can cause an unclean surface condition along portions of the exterior, patient-interfacing fabric/material of the medical device.

For strap-based medical devices, prior to its next user the strap thus needs to be taken apart and washed or wiped off with only suggested antimicrobial spray. It is, however, clearly not sustainable to abide by the cleaning instructions required by the owner's manual that such cleaning is done after every use, even though such cleaning is required pursuant the instructions of the Owner Manuals for medical devices. In fact, the Owner's Manual states, "Before somebody else will use the device, the unit and its components must be cleaned. Direct contact between the device and its application modules is only permissible on undamaged skin." The Owner's Manual further provides, regarding Care/Maintenance: "All devices and all related components are neither waterproof nor rain-proof! Do not allow moisture to penetrate into the device! Do not use any abrasive cleaners, alkaline solutions or alcohol-based cleaners!" Moreover, the disc accessory may not be sprayed with anything.

Currently, users attempts to protect their medical device (and themselves) with make-shift products or practices have at least the following problems: (1) current solutions are not properly nor accurately fitted to remain in place while using the device; and (2) current solutions provide covers made from material adapted for the required washing between use (i.e., with towels, rolled plastic, vinyl, etc.), which results in adding bulk between the patient and the medical device that needs to interface with the patient's skin as well as adding preparation time for the user and arguably overall cost.

As can be seen, there is a need for disposable covers configured for strap-based and disc-based PEMFT medical devices. The present invention embodies such disposable covers, colloquially known as the "MEDI-STRAP PROTEC"™ and the "MEDI-DISC PROTEC"™, respectively.

The PEMFT medical device covers embodied in the present invention also offer a new paradigm in the use of many medical devices, beyond medical devices, in view of the heightened global awareness of health, prevention, and safety in our world that we touch. There will be no going back.

The strap-based cover is dimensioned and adapted sleeve-like to slip on the strap-based PEMFT medical device. The strap-based cover includes custom-shaped and fitted tabs to secure it on and in place during the use of the strap-based PEMFT applicator. The strap-based cover provides a special weave of material that does not allow the above-mentioned fluids to penetrate, thereby protecting the medical device underneath and the skin of the user. The efficient design of the strap-based cover affordably allows for post-use disposal, thereby facilitating protection from bacteria and potentially the viral elements that could touch the PEMFT medical device.

The disc-based cover is dimensioned and adapted shower-cap-like to slip on the disc-based PEMFT medical device; though, the disc-based cover is designed specifically to also allow for the handles of the medical device to be exposed to be able to manually hold and manipulate the disc-based PEMFT medical device by way of the raised knob/handle, with or without a strap.

As a result, the present invention's precise design creates a custom fit on the medical device applicators, enabling an exacting, effective protective cover, fluidly sealed via the special weave of the cover material. Disposability is a time-effective solution (as compared to repeatedly cleaning reusable solution) and additionally instills absolute confidence, which increases the likelihood that patients seek this "new-age" but helpful treatment. In other words, the properties of being disposable prevents the spread of infection, diseases, bodily fluids and organisms from one patient to the next, as the covers can be applied directly on the device by the user.

SUMMARY OF THE INVENTION

In one aspect of the present invention, a pulsed electromagnetic field therapy (PEMFT) applicator covering system, the system including a fluidproof material defining a sleeve dimensioned to slidably receive and be more than coextensive with a PEMFT strap applicator; and a pair of tabs spaced apart and longitudinally extending from each end of the sleeve, wherein the pair of tabs are independently foldable against the sleeve, wherein the fluidproof material comprises spun-bound polyethylene and poly-backed wood-pulp fiber; further including a detachable fastener on a first side of each tab; and further comprising a removable layer on each detachable fastener.

In another aspect of the present invention, a pulsed electromagnetic field therapy (PEMFT) applicator covering system, the system including: a fluidproof material defining a pouch dimensioned to slidably receive at least a front portion with a PEMFT disc applicator by way of an opening in the pouch; and a pair of slots spaced apart and adjacent to the opening, wherein each slot is dimensioned to receive a handle of the received PEMFT disc applicator; further including an elastic component circumscribing the opening; further including a gathering stitching defining a channel housing the elastic component, wherein the fluidproof material comprises spun-bound polyethylene and poly-backed wood-pulp fiber.

These and other features, aspects and advantages of the present invention will become better understood with reference to the following drawings, description and claims.

BRIEF DESCRIPTION OF THE DRAWINGS

FIG. 1 is a perspective view of an exemplary embodiment of the present invention, shown in use;

FIG. 2 is a perspective view of an exemplary embodiment of the present invention;

DETAILED DESCRIPTION OF THE INVENTION

Figure 3:
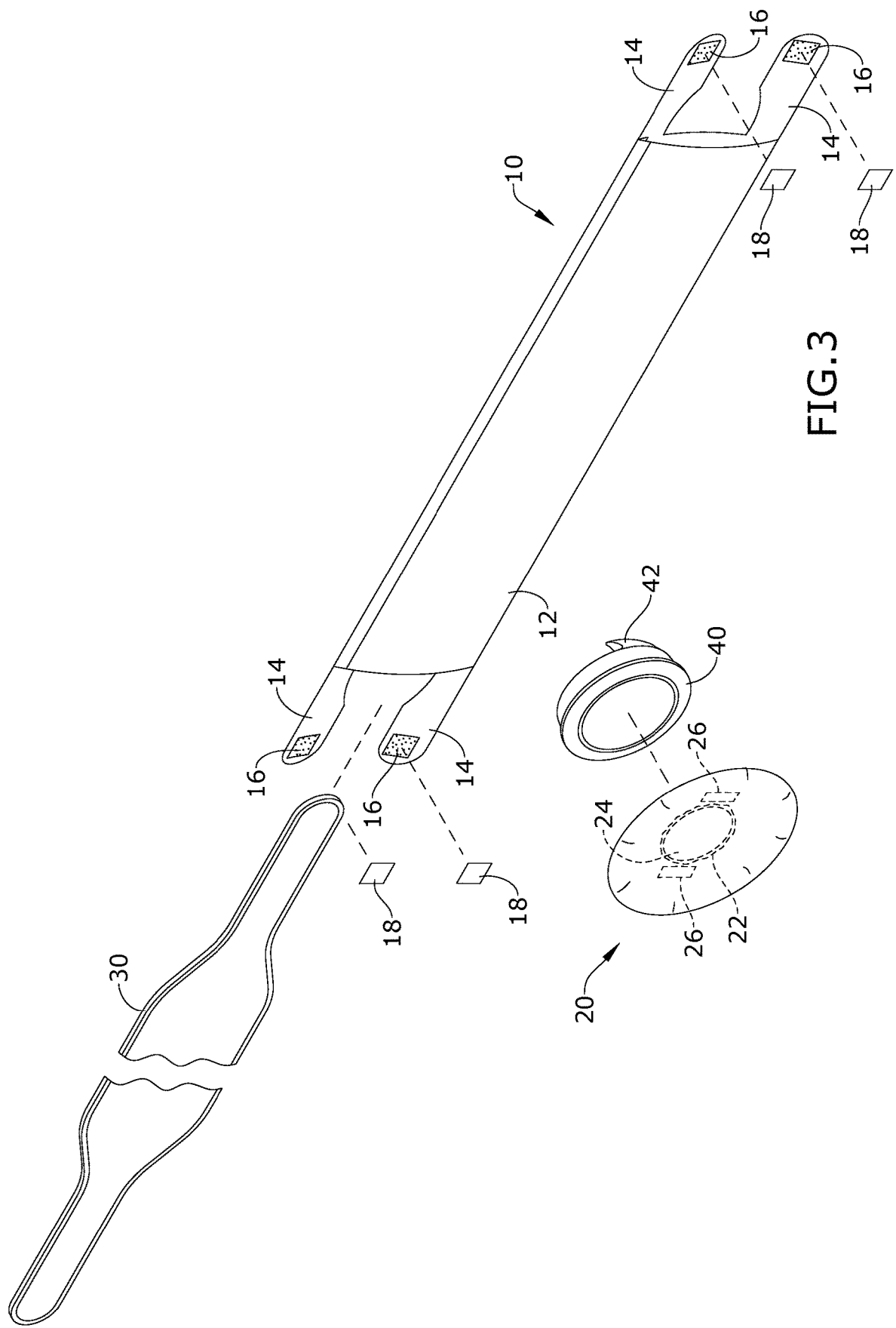
FIG. 3 is an exploded front perspective view of an exemplary embodiment of the present invention.
Figure 4:
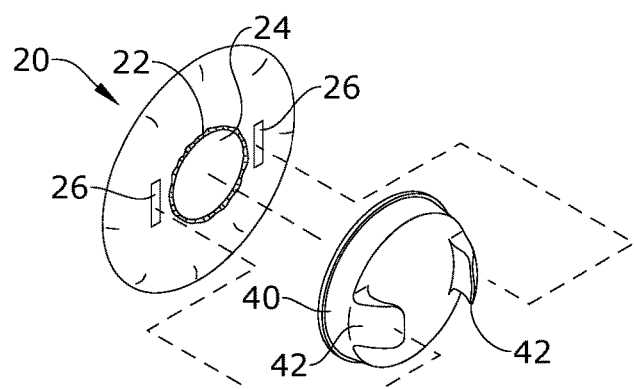
FIG. 4 is an exploded rear perspective view of an exemplary embodiment of the present invention, illustrating the disc application and covering; specifically the placement of slots 26 over handles 42.
Figure 5:
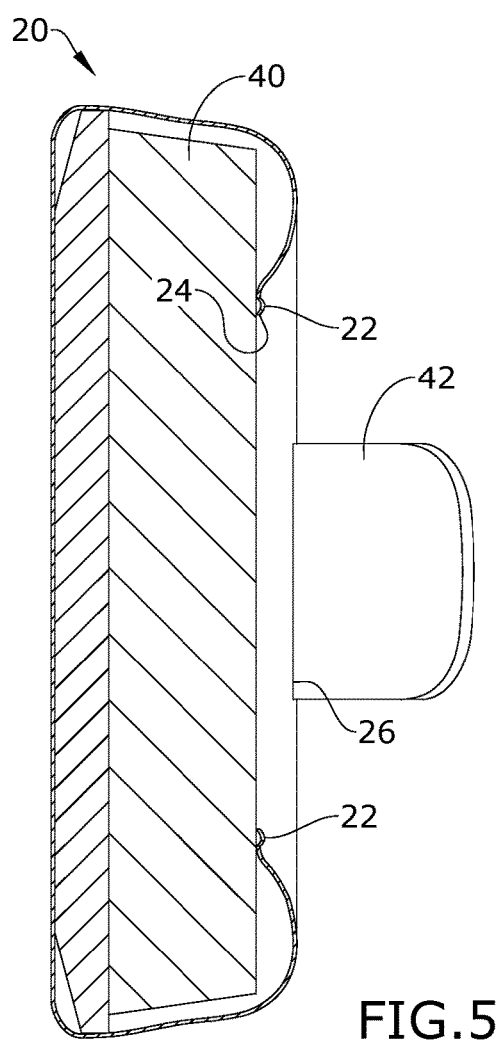
FIG. 5 is a section view of an exemplary embodiment of the present invention, taken along line 5-5 in FIG. 1.
Figure 6:
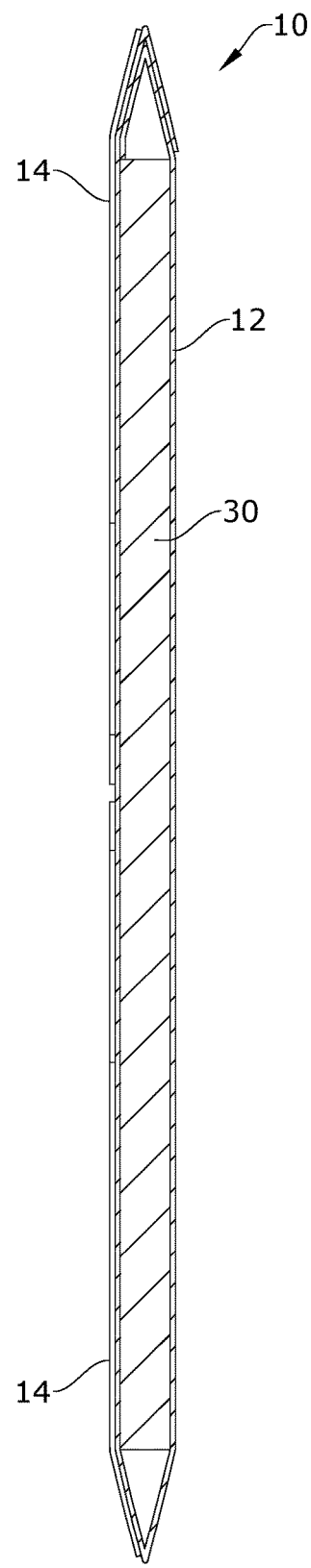
FIG. 6 is a section view of an exemplary embodiment of the present invention, taken along line 6-6 in FIG. 1.

The following detailed description is of the best currently contemplated modes of carrying out exemplary embodiments of the invention. The description is not to be taken in a limiting sense but is made merely for the purpose of illustrating the general principles of the invention, since the scope of the invention is best defined by the appended claims.

Broadly, an embodiment of the present invention provides custom disposable medical device covers. The covers may be made from spun-bound polyethylene and poly-backed wood-pulp fiber ("cover material") cut into a design pattern that is then formed to custom fit PEMFT medical devices. The cover material may include 50 gsm spunlace laminate fabric. The final design may be facilitated by the way of polyester/cotton blend or nylon thread, an elastic component, and detachable fasteners, such as but not limited to hook and loop fasteners and/or restickable tape on tab closures.

Referring to FIGS. 1 through 9, the present invention may include (1) a strap cover 10 for (strap-based PEMFT medical devices or) strap applicators 30; and (2) a disc cover 20 for (disc-based PEMFT medical devices or) disc applicators 40.

Figure 7A:
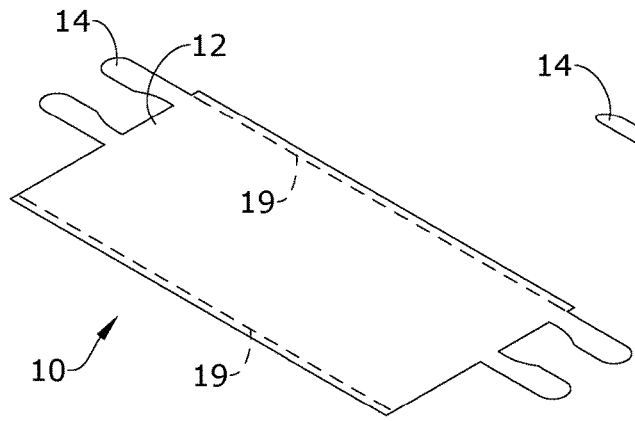
FIG. 7A is a perspective view of an exemplary embodiment of the present invention, illustrating the flat pattern for strap cover 10.
Figure 7B:
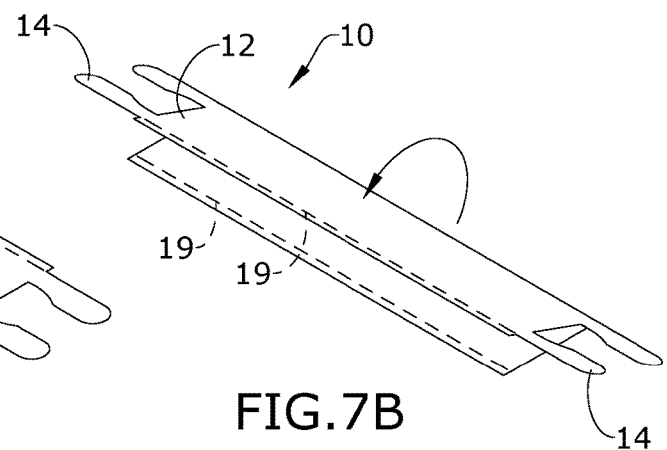
FIG. 7B is a perspective view of an exemplary embodiment of the present invention, illustrating the strap cover 10, showing the center fold before sewing seam 19.

The strap cover 10, 50 may be formed from the cover material that is cut into a flat strap pattern, as illustrated in FIG. 7A, which may be sewn with a stitch down the length of the body of the strap cover 10, 50 creating a wide sleeve 12, 52 later to be creased along one longitudinal edge to form a seam with the opposing edge along a seam line 19. Tabs 14, 54 (cutout flaps) may longitudinally extend from an upper and lower edges of both ends of the sleeve 12, 52. Each tab 14, 54 may extend for five inches. Each tab 14, 54 may be substantially rectangular or oval with a tapered portion at the edge of the sleeve 12, as illustrated in FIG. 3. Detachable fasteners 16 may be connected to the same side of the tabs 14. Each detachable fastener 16 may have a removable layer 18.

The disc cover 20 may be formed from the cover material that is cut into a pouch-shaped disc pattern having an opening 24, wherein an elastic component 22 is sewn into a periphery defining the opening 24 by way of gathering stitching 21. The elastic component may have a 14-inch thickness in certain embodiments, Slots 26 may be provided adjacent to the opening 24. Each slot 26 may be dimensioned and adapted to slidably receive the handles 42 of the disc applicator 40.

The strap cover 10, 50 works by completely siding over (like a pillowcase) and covering the effective usage area of the strap applicator 30. Then, the two end tabs 14, on each end of the sleeve 12, are then folded over, removing the removable layer 18, and conveniently joining the detachable fastener 16 to the surface of the strap cover 10. 54 flaps, without stick pads, are alternatively tucked down inside front sheath of 50 body. Now the entire usage area of the strap applicator 30 is protected and protects the user from making contact with undesirable or unclean particles. After use, the strap cover 10, 50 may be disposed of, and a new one used for the next user.

The disc cover 20 works by stretching out the elastic component and placing it over the top/face of the disc applicator 40, much like a shower cap, bringing it all the way up the sides so that the two handles 42 protrude from the slots 26. The biasing of the elastic component 22 urges an associated portion of the body of the disc cover 20 snugly against the rear surface of the disc applicator 40. A portion of the disc applicator 40 protrudes through the opening 24 for application purposes. The gathering stitch 21 enables this functionality through forming a channel housing the elastic component 22. As a result, during use of the disc applicator 40, the cover material contacts the skin area being treated, and the hand that holds the disc applicator 40 will be protected. Thereafter, the disc cover 20 may be disposed of, and a new one used for the next user.

A method of manufacturing the present invention may include the following. To make the strap cover 10, 50 a manufacturer may cut the pattern out of the selective grade "cover material" designed perfectly to fit the medical device it is designed to protect. A person skilled in the art will calculate the fabric dimensions based on the relevant strap applicator 30. In certain embodiments, approximately 26 inches in length and 13 inches in width for the sleeve 12, 52.

Figure 8A:
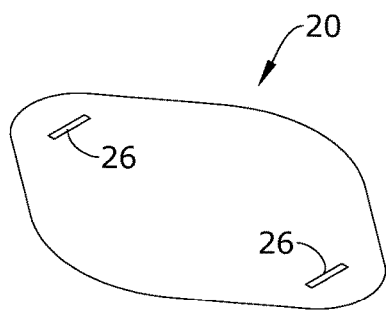
FIG. 8A is a perspective view of an exemplary embodiment of the present invention, illustrating the flat pattern for disc cover 20.
Figure 8B:
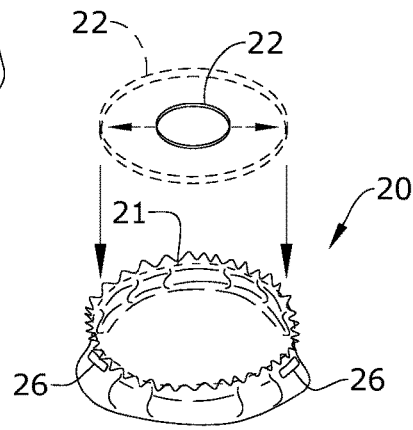
FIG. 8B is a perspective views of an exemplary embodiment of the present invention, illustrating the disc cover 20, showing it gathered by the basting stich and illustrating the placement of elastic 22 to be stitched in place.
Figure 8C:
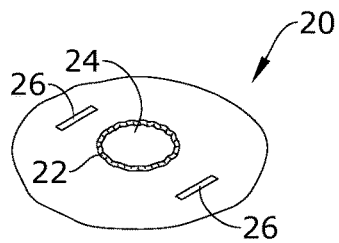
FIG. 8C is a perspective view of an exemplary embodiment of the present invention, illustrating the disc cover 20 with elastic 22 sewn in place to create opening 24.

A method of manufacturing the disc cover 20 may include cutting the cover material fabric into the (die cut) flat disc pattern shown in FIG. 8A. The disc pattern is sewn all around the outer edge with, in certain embodiments, a basting stitch using a gather presser foot, creating a 'balloon' with a 6" to 7" opening 24. The approximately 5½" elastic component 22 may have been pre-made into a 5" circle with ¼" overlap fix stitch. This circular elastic component 22 may be placed and stretched over the 'balloon' opening and laid down with a basting zig-zag stitch (100% nylon thread) no wider than the ¼" elastic component 22, thereby creating the disc cover 20. This exacting procedure creates a consistent opening and closing function and size of 20.

The manufacturer would then sew a seam allowance using a polyester/cotton blend thread or the like with, in certain embodiments, an approximately #3 stitch width (using approximately eight stitches per inch). The seam may be 26-inches long. The sleeve 12, 52 may then be turned right side out and pressed flat leaving crease at top/seam at bottom of the finished sleeve 12, 52, having an approximately six-inch width. The manufacturer may affix the peelable layer 18 over the detachable fasteners 16.

The components of the strap cover 10, that could be reconfigured to cause the present invention to perform a similar function, wherein the flaps 14 at each end of the approximately 26-inch sleeve body that are on opposite sides of the 'sleeve' and are alternatively placed to face inward towards each other.

Figure 9:
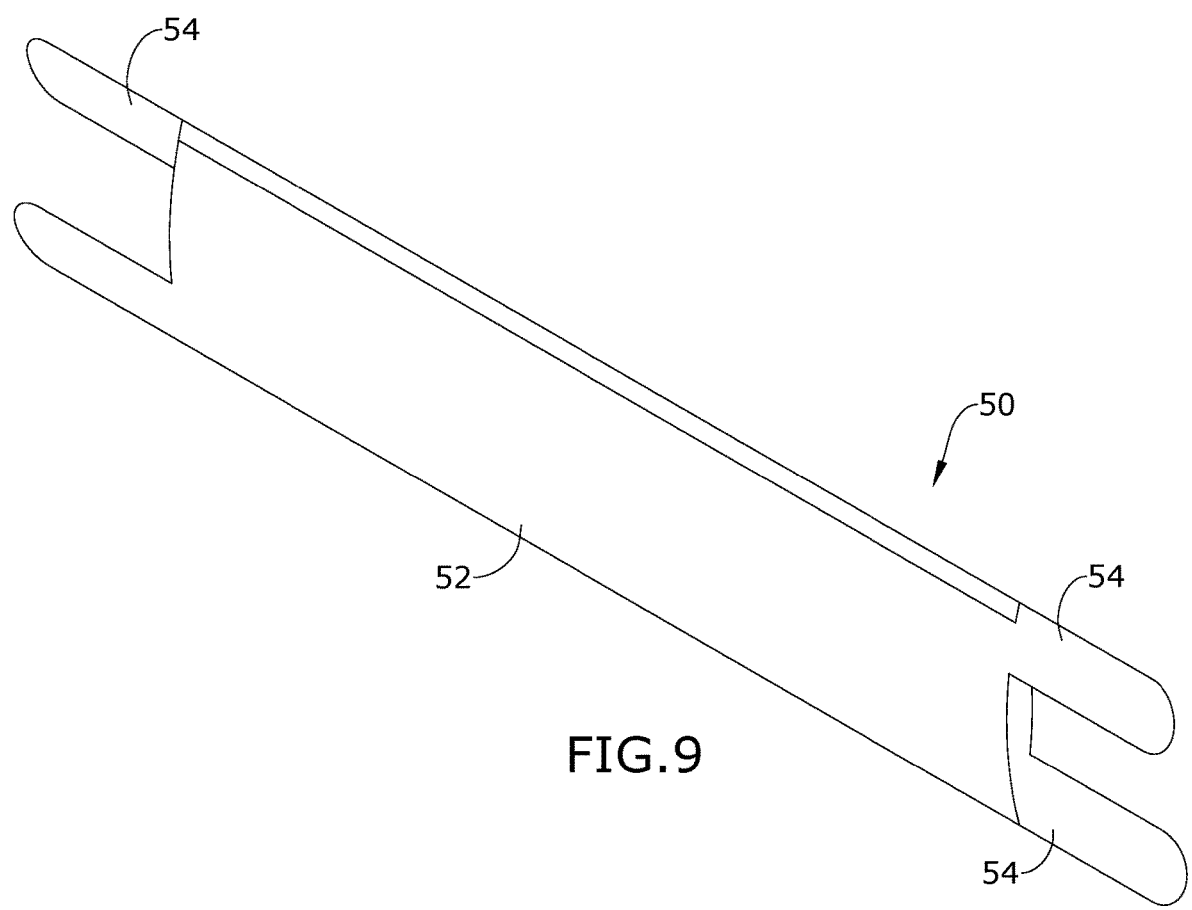
FIG. 9 is a perspective view of an exemplary other embodiment of the present invention.

In certain embodiments, the flaps 54, as illustrated in FIG. 9, could function by simply being tucked into a 'pocket' slit underneath where the PEMF coils reside.

It should be understood, of course, that the foregoing relates to exemplary embodiments of the invention and that modifications may be made without departing from the spirit and scope of the invention as set forth in the following claims.

What is claimed is:

1. A pulsed electromagnetic field therapy (PEMFT) applicator covering system, the system comprising:
   a fluidproof material defining a sleeve dimensioned to slidably receive a PEMFT strap applicator;
   a pair of tabs spaced apart and longitudinally extending from each end of the sleeve, wherein the pair of tabs are independently foldable against the sleeve, wherein the fluidproof material comprises spun-bound polyethylene and poly-backed wood-pulp fiber; and
   detachable fastener on a first side of each tab.

2. The system of claim 1, further comprising a removable layer on each detachable fastener.

3. A pulsed electromagnetic field therapy (PEMFT) applicator covering system, the system comprising:
   a fluidproof material defining a pouch-shaped disc pattern dimensioned to slidably receive at least a front portion with a PEMFT disc applicator by way of an opening in the pouch-shaped disc pattern;
   a pair of slots spaced apart and adjacent to the opening, wherein each slot is dimensioned to receive a handle of the received PEMFT disc applicator; and
   an elastic component circumscribing the opening.

4. The system of claim 3, further comprising a gathering stitching defining a channel housing the elastic component.

5. The system of claim 4, wherein the fluidproof material comprises spun- bound polyethylene and poly-backed wood-pulp fiber.

* * * * *